(12) United States Patent
Fan et al.

(10) Patent No.: US 11,577,070 B2
(45) Date of Patent: *Feb. 14, 2023

(54) SOFT PHYSIOTHERAPY INSTRUMENT

(71) Applicant: Beijing FUNATE Innovation Technology Co., LTD., Beijing (CN)

(72) Inventors: Li Fan, Beijing (CN); Li Qian, Beijing (CN); Yu-Quan Wang, Beijing (CN)

(73) Assignee: Beijing FUNATE Innovation Technology Co., LTD., Beijing (CN)

( * ) Notice: Subject to any disclaimer, the term of this patent is extended or adjusted under 35 U.S.C. 154(b) by 234 days.

This patent is subject to a terminal disclaimer.

(21) Appl. No.: 17/036,398

(22) Filed: Sep. 29, 2020

(65) Prior Publication Data

US 2021/0213278 A1 Jul. 15, 2021

(30) Foreign Application Priority Data

Jan. 15, 2020 (CN) .......................... 202010043624.7

(51) Int. Cl.
| | | |
|---|---|---|
| *B32B 9/04* | (2006.01) | |
| *A61N 1/04* | (2006.01) | |
| *A61N 1/36* | (2006.01) | |
| *B32B 5/26* | (2006.01) | |

(52) U.S. Cl.
CPC ......... *A61N 1/0484* (2013.01); *A61N 1/0472* (2013.01); *A61N 1/36014* (2013.01); *B32B 5/26* (2013.01); *B32B 9/04* (2013.01); *B32B 2255/02* (2013.01); *B32B 2255/20* (2013.01); *B32B 2262/106* (2013.01); *B32B 2437/00* (2013.01)

(58) Field of Classification Search
CPC .. A61N 1/0408; A61N 1/0472; A61N 1/0476; A61N 1/0484; A61N 1/328; A61N 1/36014; A61N 1/0492; B82Y 30/00; B32B 5/26; B32B 5/2255; B32B 5/02; B32B 5/20; B32B 2262/106
USPC ......................................................... 442/117
See application file for complete search history.

(56) References Cited

U.S. PATENT DOCUMENTS

| | | | |
|---|---|---|---|
| 11,260,217 B2 * | 3/2022 | Fan ...................... | A61N 1/0408 |
| 2010/0191316 A1 | 7/2010 | Buhlmann et al. | |
| 2018/0099143 A1 | 4/2018 | Kim et al. | |
| 2019/0336787 A1 | 11/2019 | Kweon et al. | |

FOREIGN PATENT DOCUMENTS

| | | |
|---|---|---|
| CN | 107206390 | 9/2017 |
| CN | 108159563 | 6/2018 |
| CN | 208838309 | 5/2019 |
| TW | M424059 | 3/2012 |
| WO | 2012106735 | 8/2012 |
| WO | 2015040583 | 3/2015 |
| WO | 2016016015 | 2/2016 |

* cited by examiner

*Primary Examiner* — Matthew D Matzek
(74) *Attorney, Agent, or Firm* — ScienBiziP, P.C.

(57) ABSTRACT

A soft physiotherapy instrument includes a flexible sheet and a controller. The flexible sheet includes a first flexible layer, a second flexible layer, a plurality of functional layers located between the first flexible layer and the second flexible layer, and a plurality of electrodes electrically connected with the plurality of functional layers. The functional layer includes a carbon nanotube layer including a plurality of carbon nanotubes uniformly distributed. The flexible sheet is electrically coupled with the controller via the plurality of electrodes.

16 Claims, 14 Drawing Sheets

SOFT PHYSIOTHERAPY INSTRUMENT

CROSS-REFERENCE TO RELATED APPLICATIONS

The application is also related to copending applications entitled, "MASK-TYPE BEAUTY INSTRUMENT", filed Sep. 29, 2020 (Ser. No. 17/036,341); "METHOD FOR USING MASK-TYPE BEAUTY INSTRUMENT", filed Sep. 29, 2020 (Ser. No. 17/036,354); "METHOD FOR USING SOFT PHYSIOTHERAPY INSTRUMENT," filed Sep. 29, 2020 (Ser. No. 17/036,425).

FIELD

The subject matter herein generally relates to a soft physiotherapy instrument.

BACKGROUND

With the continuous improvement of people's material living standards, people's demand for health is also increasing. Following this, various physiotherapy products are sell well. Most of the physiotherapy products on the market are made of hard materials, and the area that acts on the human body is also small, and the human body is not comfortable.

BRIEF DESCRIPTION OF THE DRAWINGS

Implementations of the present technology will now be described, by way of embodiments, with reference to the attached figures, wherein.

DETAILED DESCRIPTION

Figure 1:
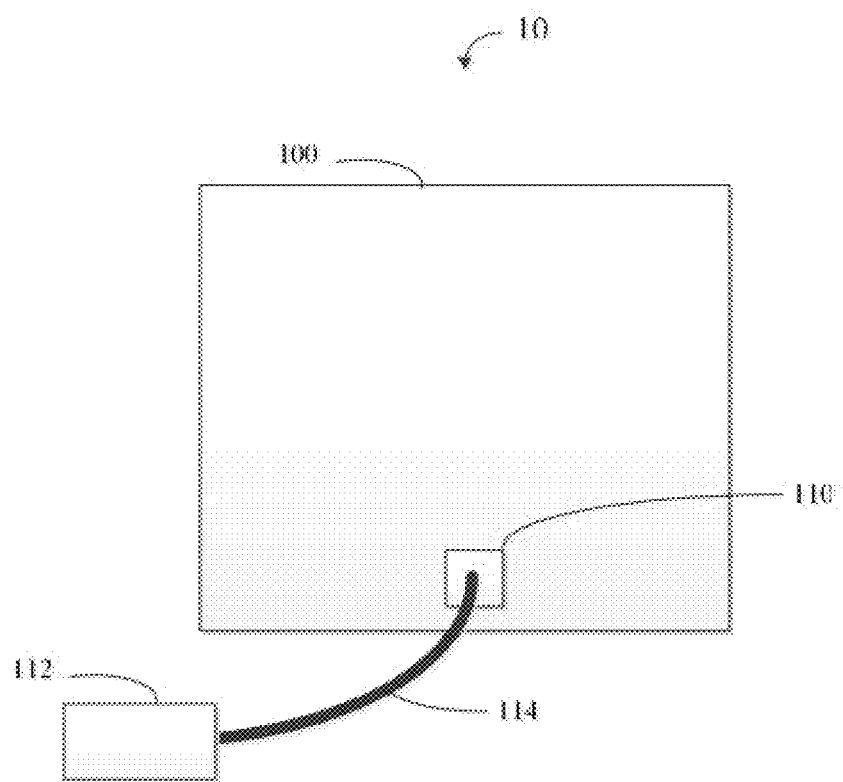
FIG. 1 is a schematic view of a soft physiotherapy instrument according to a first embodiment.

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "contact" is defined as a direct and physical contact. The term "substantially" is defined to be that while essentially conforming to the particular dimension, shape, or other feature that is described, the component is not or need not be exactly conforming to the description. The term "comprising," when utilized, means "including, but not necessarily limited to"; it specifically indicates open-ended inclusion or membership in the so-described combination, group, series, and the like.

Figure 2:
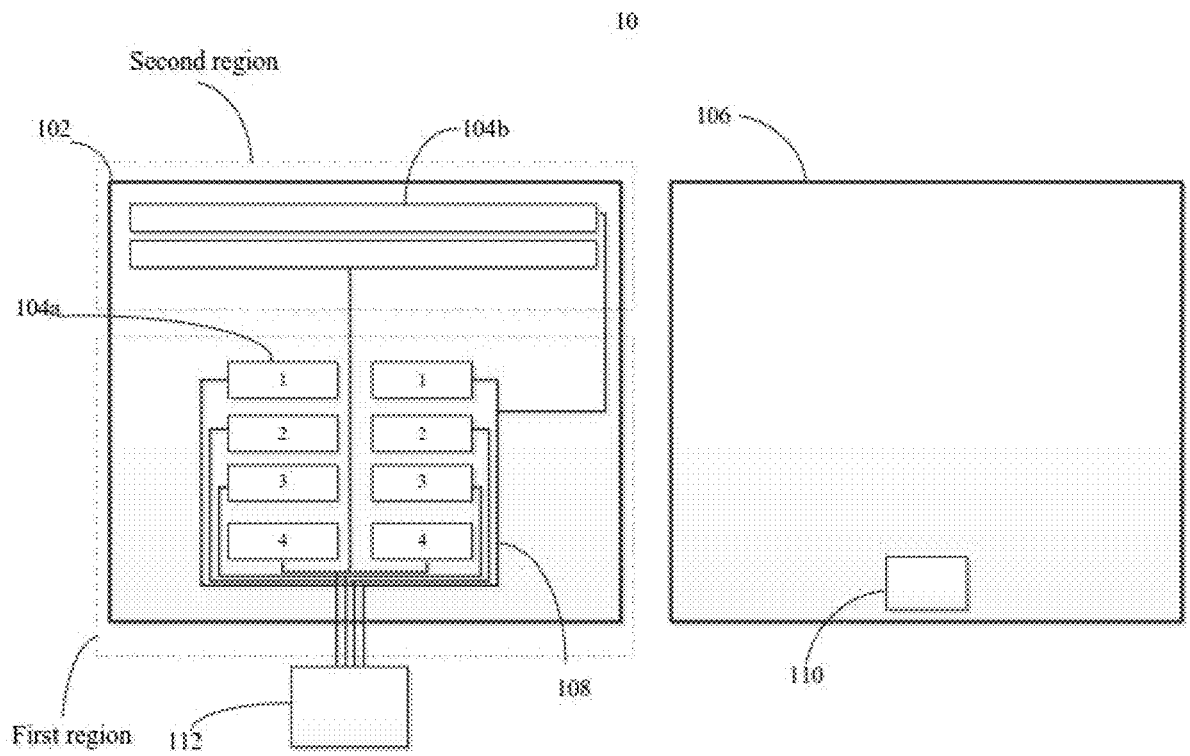
FIG. 2 is a schematic view of an internal structure of the soft physiotherapy instrument in FIG. 1.

Referring to FIGS. 1 and 2, a soft physiotherapy instrument 10 according to a first embodiment is provided. The soft physiotherapy instrument 10 includes a flexible sheet 100, a controller 112 and a connection wire 114, the controller 112 is used for controlling the flexible sheet 100 via the connection wire 114. The controller 112 is movably connected with the flexible sheet 100 via the connection wire 114. The flexible sheet 100 includes a first flexible layer 102 and a second flexible layer 106 overlapped with each other (for clarity of display, in FIG. 2, the first flexible layer 102 and the second flexible layer 106 are separately shown), the first flexible layer 102 and the second flexible layer 106 have corresponding eye and mouth openings (not labeled). The flexible sheet 100 further includes a plurality of functional layers 104 sandwiched between the first flexible layer 102 and the second flexible layer 106, the plurality of functional layers 104 are symmetrically distributed or regularly distributed, and a plurality of electrodes 108, each of the plurality of electrodes 108 is electrically connected with a single functional layer 104 or a pair of functional layers 104. The controller 112 is electrically connected with the plurality of electrodes 108 via the connection wire.

The flexible sheet 100 defines a first region (not labeled) and a second region (not labeled). The plurality of functional layers 104 comprises a plurality of first functional layers 104a and a plurality of second functional layers 104b. The plurality of first functional layers 104a are located in the first region. The plurality of second functional layers 104b are located in the second region. A quantity of the first functional layers 104a is 2K, a quantity of the second functional layers 104b is M, and K is greater than or equal to M. The 2K first functional layers 104a are symmetrically distributed on the first region of flexible sheet 100. Each pairs of first functional layers 104a are symmetrically distributed at a left column and a right column and are electrically connected with one electrode 108 of the plurality of electrodes 108. That is, K first functional layers 104a are located at the left column, the other K first functional layers 104a are located at the right column. And, a quantity of the plurality of electrodes 108 is K. Each of the plurality of electrodes 108 is numbered as 1, 2, 3 . . . K, and two electrodes with adjacent numbers are electrically connected with adjacent pairs of first functional layers 104a. A quantity of pairs of the first functional layers 104a is the same as the quantity of the electrodes 108, and number of each pair of the first functional layers 104a is the same as the number of electrode 108 electrically connected with the pair of first functional layers 104a. Each of the plurality of second functional layers 104b is electrically connected with one electrode. Numbers of two electrodes electrically connected with adjacent second functional layers 104b is x and y, and a difference between x and y is greater than or equal to 2.

Areas of the plurality of functional layers can be different and can be adjusted as required. In the embodiment according to FIGS. 1 and 2, the quantity of plurality of first functional layers 104a is 8, of which the 8 first functional layers 104a are symmetrically distributed in the first region of the flexible facial mask 100; and 2 second functional layers 104b are located in the second region of the flexible facial mask 100. Each electrode 108 is numbered 1, 2, 3, and 4 in order from the left to the right of the end position connected to the controller 112, corresponding to the number of the electrode 108, and each pair of symmetrical main functional layers 104a are sequentially numbered from top to bottom of the flexible facial mask 100. In the second region, one of the second functional layers 104b is electrically connected to the electrode 108 numbered 1, and the other functional layer 104b is connected to the electrode numbered 4. That is, the difference between x and y is 3.

The controller 112 is configured to control the plurality of functional layers 104 in the flexible sheet 100 through the K electrodes 108. The K electrodes extend from the inside of the flexible facial mask 100 and converge in the connection wire 114, and the controller 112 is connected with the flexible sheet 100 through the connection wire 114. The controller 112 comprises a plurality of buttons for controlling the flexible sheet 100. The controller 112 is used to input a voltage between two of the plurality of electrodes 108 to produce current in the plurality of functional layers 104. A circuit is formed between the controller, the two of the plurality of electrodes 108, the plurality of functional layers 104 electrically connected with the two of the plurality of electrodes 108, and the skin of the user. As such, the current flows through the controller, the two of the plurality of electrodes 108, the plurality of functional layers 104 electrically connected with the two of the plurality of electrodes 108, and the skin of the user. Each of the plurality of function buttons can control the current magnitude, the frequency of the current, the position of the input current, etc., to control the plurality of functional layers 104 inside the flexible sheet 100. The flexible sheet 100 can be movably coupled to the controller 200. Optionally, the first flexible layer 102 or the second flexible layer 106 can include a window 110, and the plurality of electrodes 108 a first electrode lead 114 and a second electrode lead 116 are exposed from the window 110 and electrically connected to the controller 200 via a plurality of lead wires 108a. The window 110 is provided with an access port through which the controller 200 is connected to the flexible sheet 100. The flexible sheet 100 can be replaced as needed. The flexible sheet 100 can also be cleaned for reuse.

The K electrodes 108 are electrically connected to the K pairs of first functional layers 104a, and at the same time, are electrically connected to the M second functional layers 104b. This connection mode does not require additional electrodes to be electrically connected to the M second functional layers 104b except the K electrodes 108. The quantity of electrodes 108 is saved. Since the K electrodes 108 extend from the flexible sheet 100 and converge in the connection wire 114, the diameter of the connection wire 114 can be small. It can be understood that the smaller the diameter of the connection wire 114, the better the flexibility of the connection wire 114. The flexible sheet 100 and the controller 112 are connected by the connection wire 114. The better the flexibility of the connecting wire 114, the better the user experience.

Each of the plurality of electrodes 108 is electrically connected with a pair of first functional layers 104a. In use of the soft physiotherapy instrument 10, the flexible sheet 100 is applied on a user's skin, and a voltage is applied to two electrodes 108, the voltage is applied between the two electrodes 108 in cycles of 1 and 2, 2 and 3, 3 and 4 . . . K−1 and K, so as to circulate the two pairs of first functional layers 104a corresponding to each two electrodes 108. A loop is formed between the controller 112, the two electrodes 108, two pairs of first functional layers 104a, the skin of the user between the two first functional layers 104a on one side, the skin of the user between the two first functional layers 104a on the other side. A current is generated in the loop, as such, the skin of the user between the two first functional layers 104a on one side and the skin of the user between the two first functional layers 104a on the other side are stimulated. The two electrodes 108 with two neighbor number, e.g., K−1 and K, are connected with the two pair of first functional layer 104a, wherein the two functional layers 104a on the same side are located adjacent with each other and named adjacent functional layers, and there is no other functional layer 104a located between the adjacent functional layers on the same side. The user's skin located between the adjacent functional layers is stimulated. In this way, by sequentially or selectively applying voltage to the two electrodes 108 with adjacent numbers, the purpose of sequentially or selectively stimulating the skin of the user at different positions in the first region can be achieved.

The controller 112 can also input a voltage between two electrodes 108 that are not adjacent in number. When the difference between the numbers x and y of the two electrodes 108 is greater than or equal to 2, the two pairs of first function layers 104a corresponding to the two electrodes 108 comprises two first functional layers 104a on the same side separated with each other. The two first functional layers 104a on the same side is separated by at least one first functional layer 104a on the same side of the flexible sheet 100. Even if a loop is formed between the controller 112, the two electrodes 108, two pairs of first functional layers 104a, the skin of the user between the two first functional layers 104a on one side, the skin of the user between the two first functional layers 104a on the other side, since the two first functional layers 104a are farther apart on the same side of the flexible sheet 100, the skin between the two first functional layer 104a has a large area, the electrical resistance of the skin is relatively large, and the current generated at this time will be very small, and the user basically cannot feel it. On the other hand, when the two electrodes 108 numbered x and y are respectively connected to two second functional layers 104b, input voltage on the two electrodes 108, then another loop is formed between the two electrodes 108, the two second functional layers 104b, the facial skin between the two second functional layers 104b and the controller 112. Since the two electrically connected second functional layers 104b are adjacent to each other, the current value is relatively large, which can stimulate the skin between the two secondary functional layers 104b. As such, the skin in the second area is stimulated. Therefore, when the controller 112 chooses to apply a voltage between two electrodes 108 that have numbers not adjacent, it will not stimulate the skin between the first functional layers 104a in the first region, but it can stimulate the skin between the second functional layers 104b in the second region.

A material of the first flexible layer 102 or the second flexible layer 106 can be a flexible material such as non-woven fabric, silk, flexible cloth, porous flexible paper, or silica gel, and can be directly attached to a person's skin. A thickness of the first flexible layer 102 or the second flexible layer 106 can be set according to actual needs. In this embodiment, the thickness of the first flexible layer 102 or the second flexible layer 106 is in a range from 10 to 100 micrometers. In use of the soft physiotherapy instrument, the second flexible layer 106 will be directly attached on a skin. The second flexible layer 106 can have a porous structure.

Figure 3:
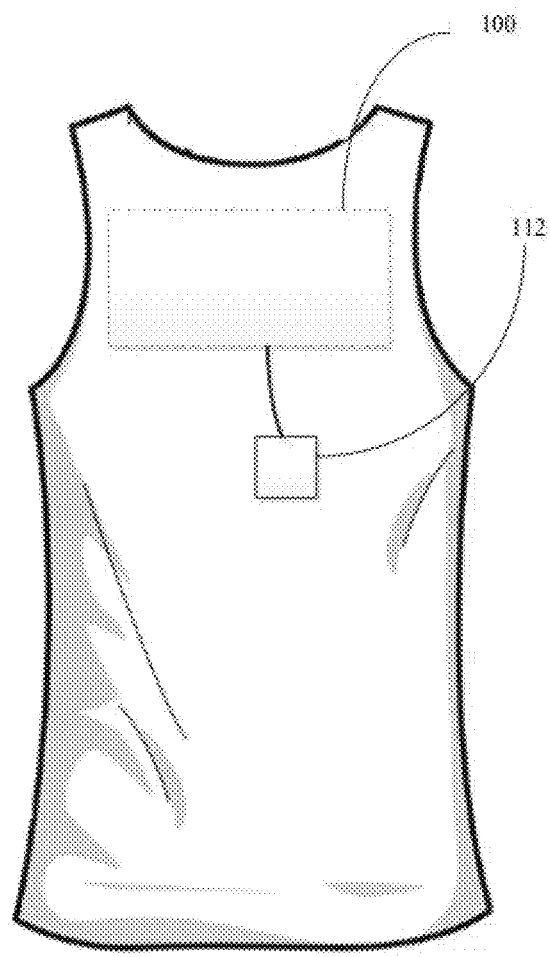
FIG. 3 is a schematic view of the a soft physiotherapy instrument provided by the first embodiment applied to a clothes.

The flexible sheet 100 can be applied to any part of the human body, such as the back, legs, knees, and abdomen. The flexible sheet 100 can also be a part of clothes or other wearables. Please refer to FIG. 3, the flexible sheet 100 can be arranged on a clothes (not labeled) to serve as a shoulder and neck physiotherapy device, and the controller 112 can be built into clothing. It can be understood that, in other embodiments, the controller may also be placed outside the clothes. The flexible sheet 100 can also be directly made into clothing or other wearing objects.

A material of the electrode 108 can be metal, alloy, indium tin oxide (ITO), antimony tin oxide (ATO), conductive silver paste, conductive polymer, or conductive carbon nanotube. The metal or the alloy can be aluminum, copper, tungsten, molybdenum, gold, titanium, rhodium, palladium, iridium, or any alloy thereof. In this embodiment, the K electrodes 108 are all copper wires with a diameter of 1 micrometer. Preferably, an insulating layer can be coated on the out surface of each of the K electrodes 108. A material of the insulating layer can be a flexible material.

Each of the plurality of functional layer 104 can comprise a carbon nanotube layer or can be the carbon nanotube layer. The carbon nanotube layer includes a plurality of carbon nanotubes joined by van der Waals attractive force therebetween. The carbon nanotube layer can be a substantially pure structure of carbon nanotubes, with few impurities. The carbon nanotube layer can be a freestanding structure, that is, the carbon nanotube layer can be supported by itself without a substrate. For example, if at least one point of the carbon nanotube layer is held, the entire carbon nanotube layer can be lifted while remaining its structural integrity.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of the carbon nanotubes arranged along each different direction can be almost the same (e.g. uniformly disordered). The disordered carbon nanotube layer can be isotropic, namely the carbon nanotube layer has properties identical in all directions of the carbon nanotube layer. The carbon nanotubes in the disordered carbon nanotube layer can be entangled with each other.

The carbon nanotube layer including ordered carbon nanotubes is an ordered carbon nanotube layer. The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be selected from single-walled, double-walled, and/or multi-walled carbon nanotubes. The carbon nanotube layer may include at least one carbon nanotube film. In other embodiments, the carbon nanotube layer is composed of one carbon nanotube film or at least two carbon nanotube films. In other embodiment, the carbon nanotube layer consists one carbon nanotube film or at least two carbon nanotube films.

Figure 4:
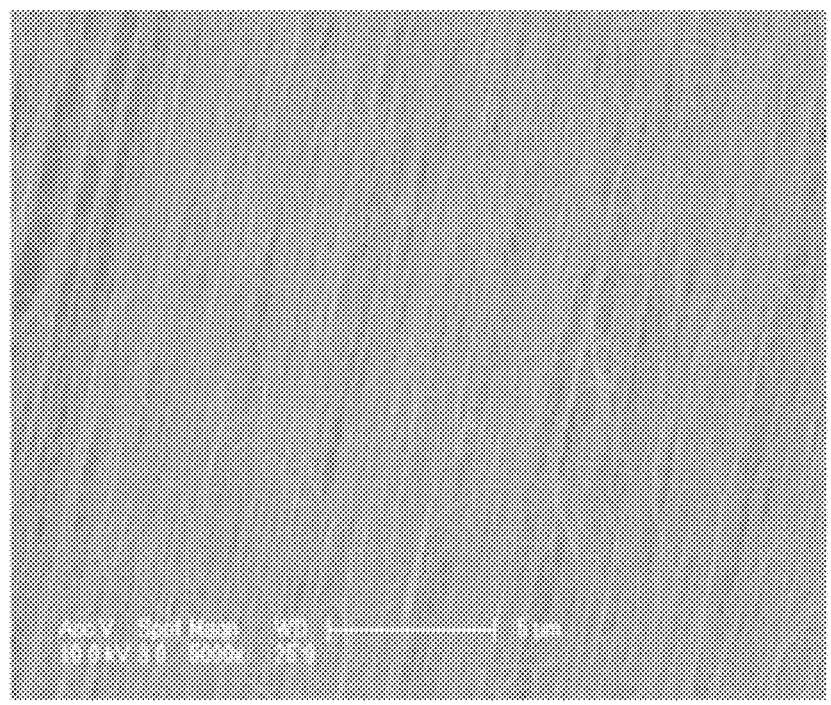
FIG. 4 shows a Scanning Electron Microscope (SEM) image of a drawn carbon nanotube film.
Figure 5:
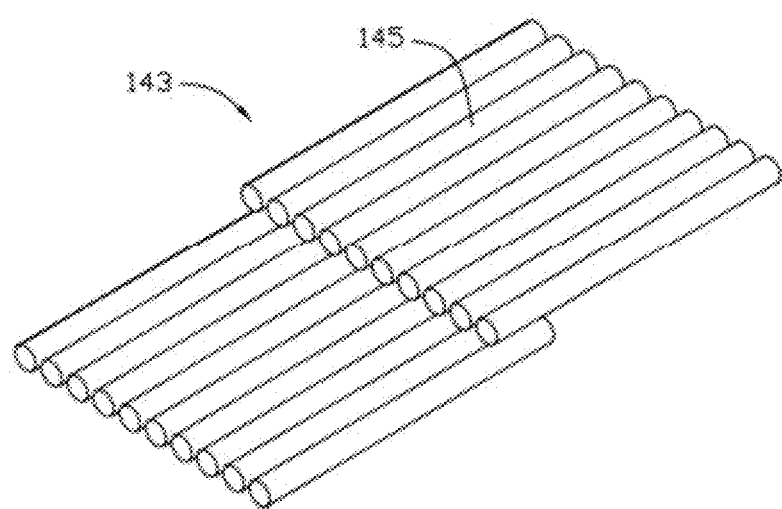
FIG. 5 is a schematic view of carbon nanotube segments in the drawn carbon nanotube film.

In one embodiment, the carbon nanotube film can be a drawn carbon nanotube film. Referring to FIG. 4, the drawn carbon nanotube film includes a number of successive and oriented carbon nanotubes joined end-to-end by van der Waals attractive force therebetween. The drawn carbon nanotube film is a freestanding film. Each drawn carbon nanotube film includes a number of successively oriented carbon nanotube segments joined end-to-end by van der Waals attractive force therebetween. Referring to FIG. 5, each carbon nanotube segment 143 includes a number of carbon nanotubes 145 substantially parallel to each other, and joined by van der Waals attractive force therebetween. Some variations can occur in the drawn carbon nanotube film. The carbon nanotubes in the drawn carbon nanotube film are oriented along a preferred orientation. The drawn carbon nanotube film can be treated with an organic solvent to increase mechanical strength and toughness of the drawn carbon nanotube film and reduce coefficient of friction of the drawn carbon nanotube film. A thickness of the drawn carbon nanotube film may range from about 0.5 nanometers to about 100 micrometers. The drawn carbon nanotube film can be used as a carbon nanotube layer directly.

The carbon nanotubes in the drawn carbon nanotube film can be single-walled, double-walled, and/or multi-walled carbon nanotubes. The diameters of the single-walled carbon nanotubes may range from about 0.5 nanometers to about 50 nanometers. The diameters of the double-walled carbon nanotubes may range from about 1 nanometer to about 50 nanometers. The diameters of the multi-walled carbon nanotubes may range from about 1.5 nanometers to about 50 nanometers. The lengths of the carbon nanotubes may range from about 200 micrometers to about 900 micrometers.

The carbon nanotube layer may include at least two stacked drawn carbon nanotube films. The carbon nanotubes in the drawn carbon nanotube film are aligned along one preferred orientation, an angle can exist between the orientations of carbon nanotubes in adjacent drawn carbon nanotube films, whether stacked or adjacent. An angle between the aligned directions of the carbon nanotubes in two adjacent drawn carbon nanotube films may range from about 0 degrees to about 90 degrees (e.g. about 15 degrees, 45 degrees, or 60 degrees).

Figure 6:
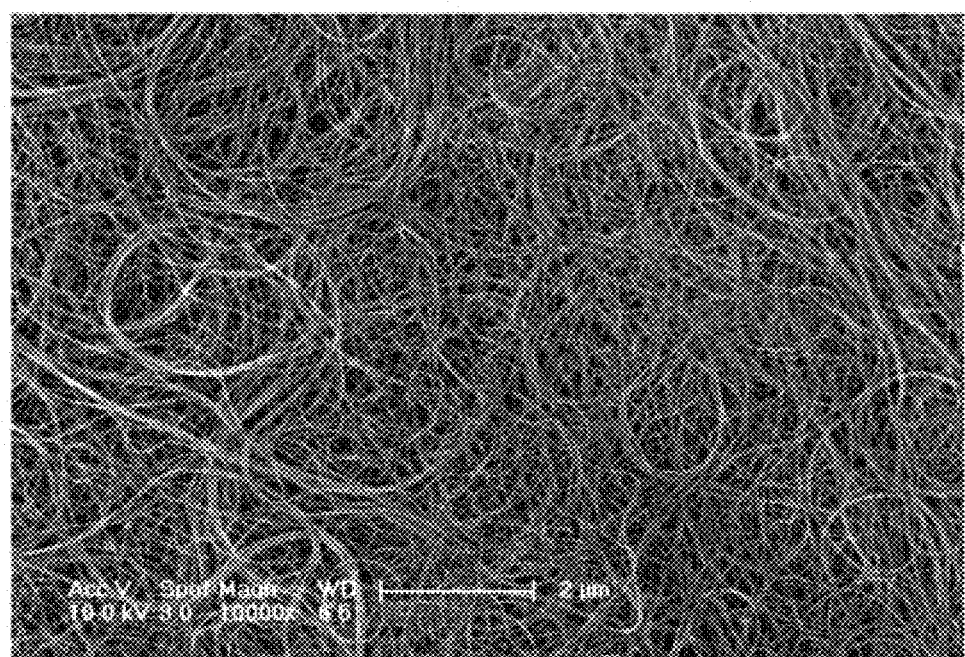
FIG. 6 shows an SEM image of a flocculated carbon nanotube film.

In other embodiments, the carbon nanotube film can be a flocculated carbon nanotube film. Referring to FIG. 6, the flocculated carbon nanotube film may include a plurality of long, curved, and disordered carbon nanotubes entangled with each other. Furthermore, the flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure with micropores defined therein. Because the carbon nanotubes in the flocculated carbon nanotube film are entangled with each other, the carbon nanotube layer employing the flocculated carbon nanotube film has excellent durability, and can be fashioned into desired shapes with a low risk to the integrity of the carbon nanotube layer. A thickness of the flocculated carbon nanotube film may range from about 0.5 nanometers to about 1 millimeter.

Figure 7:
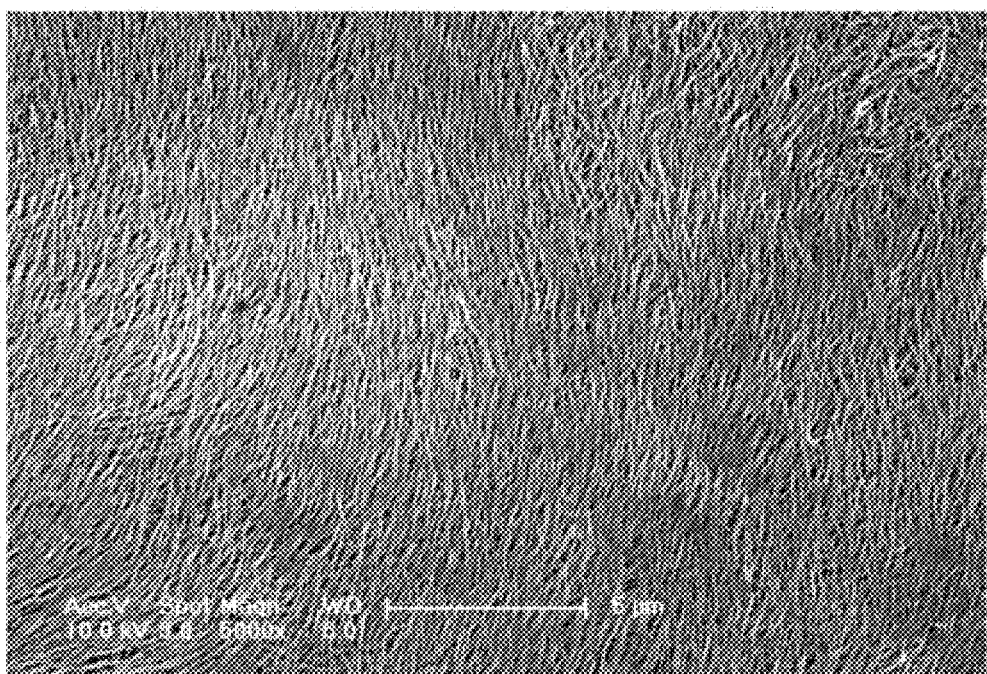
FIG. 7 shows an SEM image of a pressed carbon nanotube film.

Referring to FIG. 7, in other embodiments, the carbon nanotube film can be a pressed carbon nanotube film. The pressed carbon nanotube film is formed by pressing a carbon nanotube array. The carbon nanotubes in the pressed carbon nanotube film are arranged along a same direction or along different directions. The carbon nanotubes in the pressed carbon nanotube film can rest upon each other. Adjacent carbon nanotubes are attracted to each other and are joined by van der Waals attractive force. An angle between a primary alignment direction of the carbon nanotubes and a surface of the pressed carbon nanotube film is in a range from 0 degrees to 15 degrees. The greater the pressure applied, the smaller the angle obtained. In one embodiment, the carbon nanotubes in the pressed carbon nanotube film are arranged along different directions, the carbon nanotube layer can be isotropic. A thickness of the pressed carbon nanotube film may range from about 0.5 nanometers to about 1 millimeter.

Figure 8:
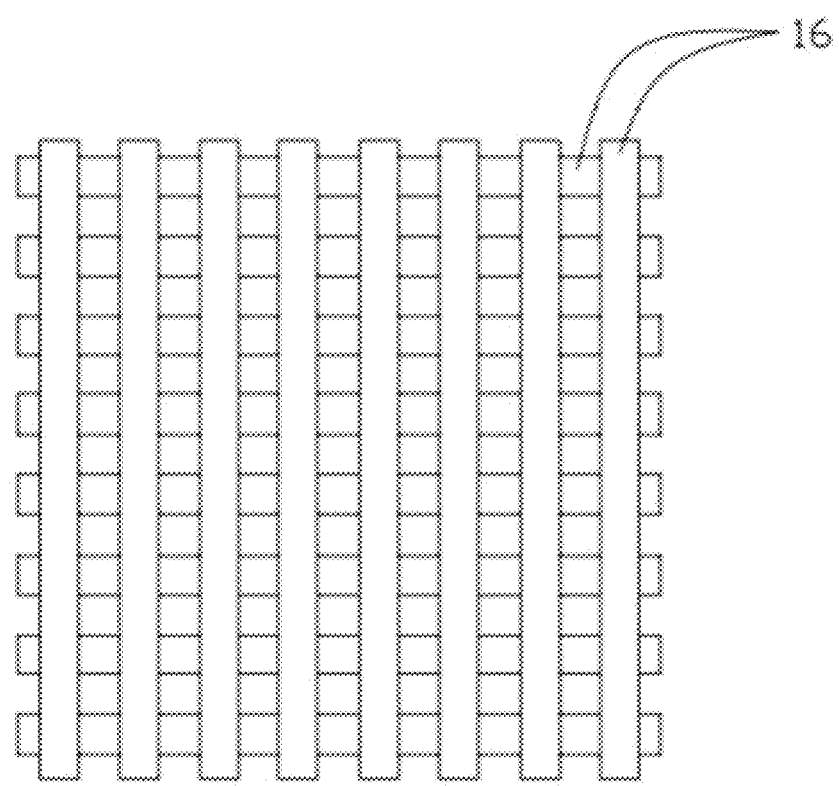
FIG. 8 is a schematic view of a functional layer including a plurality of carbon nanotube wires crossed with each other.
Figure 9:
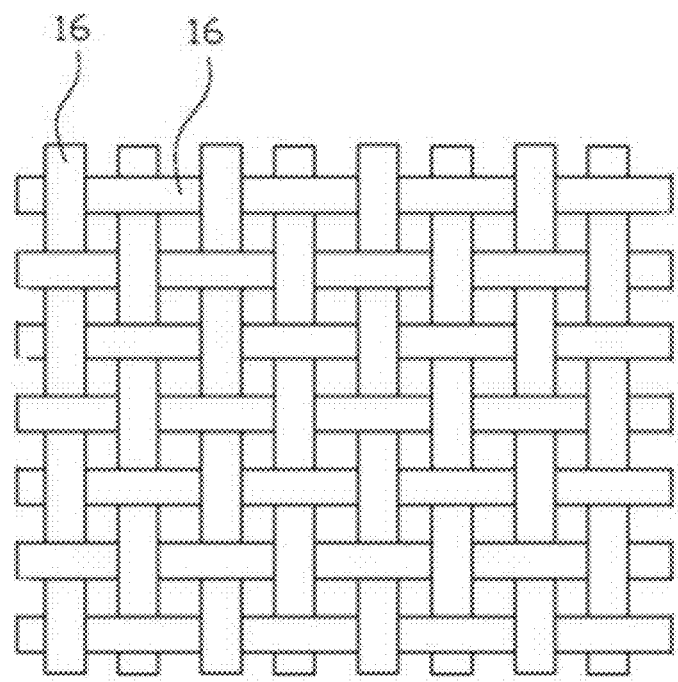
FIG. 9 is a schematic view of a functional layer including a plurality of carbon nanotube wires weaved with each other.
Figure 10:
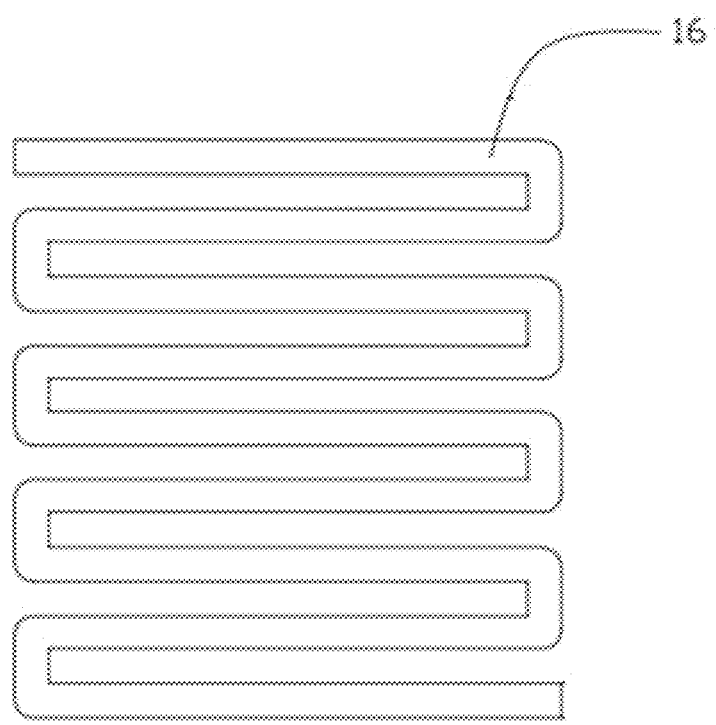
FIG. 10 is a schematic view of a functional layer including a bended and winded carbon nanotube wire.

In some embodiments, the carbon nanotube layer may include a plurality of carbon nanotube wires. Referring to FIG. 8, a plurality of carbon nanotube wires 16 can be crossed with each other to form the carbon nanotube layer. Referring to FIG. 9, a plurality of carbon nanotube wires 16 can be waved with each other to form the carbon nanotube layer. In other embodiments, the carbon nanotube layer may include only one carbon nanotube wire. Referring to FIG. 10, one carbon nanotube wire 16 can be bended to form the carbon nanotube layer.

Figure 11:
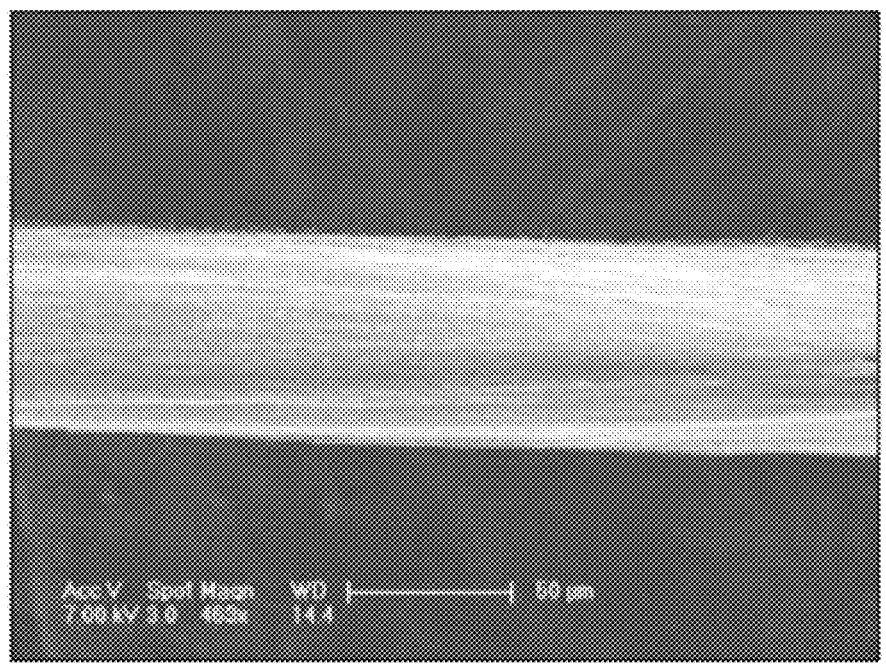
FIG. 11 is an SEM image of an untwisted carbon nanotube wire.

The carbon nanotube wire can be untwisted or twisted. Referring to FIG. 11, an untwisted carbon nanotube wire includes a plurality of carbon nanotubes substantially oriented along a same direction (i.e., a direction along the length direction of the untwisted carbon nanotube wire). The untwisted carbon nanotube wire can be a pure structure of carbon nanotubes. The untwisted carbon nanotube wire can be a freestanding structure. The carbon nanotubes are substantially parallel to the axis of the untwisted carbon nanotube wire. In one embodiment, the untwisted carbon nanotube wire may include a plurality of successive carbon nanotube segments joined end to end by van der Waals attractive force therebetween. Each carbon nanotube segment may include a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire may range from about 50 nanometers to about 100 micrometers.

Figure 12:
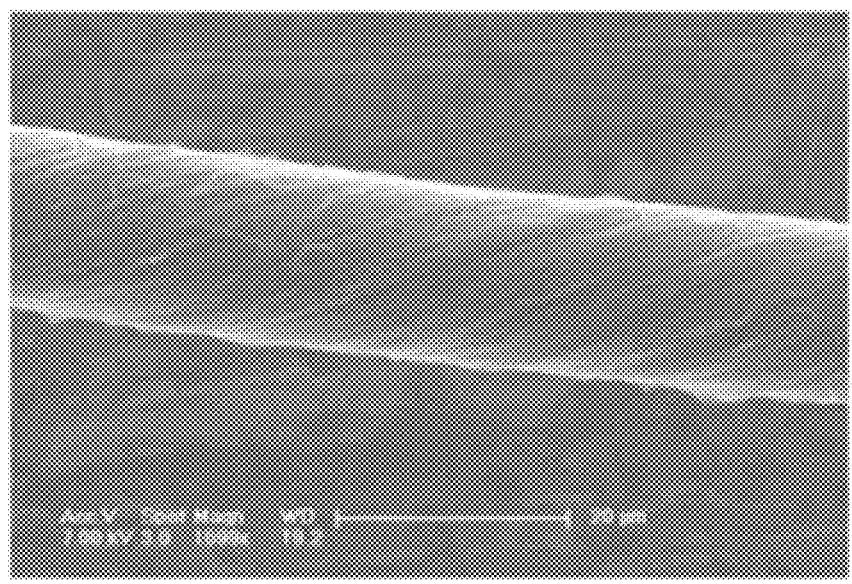
FIG. 12 is an SEM image of a twisted carbon nanotube wire.

Referring to FIG. 12, a twisted carbon nanotube wire may include a plurality of carbon nanotubes helically oriented around an axial direction of the twisted carbon nanotube wire. The twisted carbon nanotube wire can be a pure structure of carbon nanotubes. The twisted carbon nanotube wire can be a freestanding structure. In one embodiment, the twisted carbon nanotube wire may include a plurality of successive carbon nanotube segments joined end to end by van der Waals attractive force therebetween. Each carbon nanotube segment may include a plurality of carbon nanotubes substantially parallel to each other, and combined by van der Waals attractive force therebetween. The length of the carbon nanotube wire can be set as desired. A diameter of the twisted carbon nanotube wire may range from about 50 nanometers to about 100 micrometers. Furthermore, the twisted carbon nanotube wire can be treated with a volatile organic solvent after being twisted. After being soaked by the organic solvent, the adjacent substantially parallel carbon nanotubes in the twisted carbon nanotube wire will bundle together, due to a surskin tension of the organic solvent when the organic solvent volatilizes. The density and strength of the twisted carbon nanotube wire will increase.

The carbon nanotube layer has a better flexibility than the first flexible layer 102 and/or the second flexible layer 106. When the carbon nanotube layer is used as the functional layer 104 in the flexible sheet 100, the flexibility of the entire flexible sheet 100 is not decreased by the functional layer 104. The carbon nanotube layer has a large strength, as such, no matter how the flexible sheet 100 is bent or pulled, and the carbon nanotube layer is not damaged.

In other embodiment, each of the plurality of functional layer 104 can further comprise a graphene layer. The graphene layer includes at least one graphene. In one embodiment, the graphene layer is a pure structure of graphenes. The graphene layer structure can include a single graphene or a plurality of graphenes. In one embodiment, the graphene layer includes a plurality of graphenes, the plurality of graphenes is stacked with each other and/or located side by side. The plurality of graphenes is combined with each other by van der Waals attractive force. The graphene layer can be a continuous integrated structure. The term "continuous integrated structure" can be defined as a structure that is combined by a plurality of chemical covalent bonds (e.g., $sp^2$ bonds, $sp^1$ bonds, or $sp^3$ bonds) to form an overall structure. A thickness of the graphene layer can be less than 100 nanometers. The carbon nanotube layer can be overlapped with the graphene layer. The carbon nanotube layer and the graphene layer can be two separated layers overlapped with each other.

Figure 13:
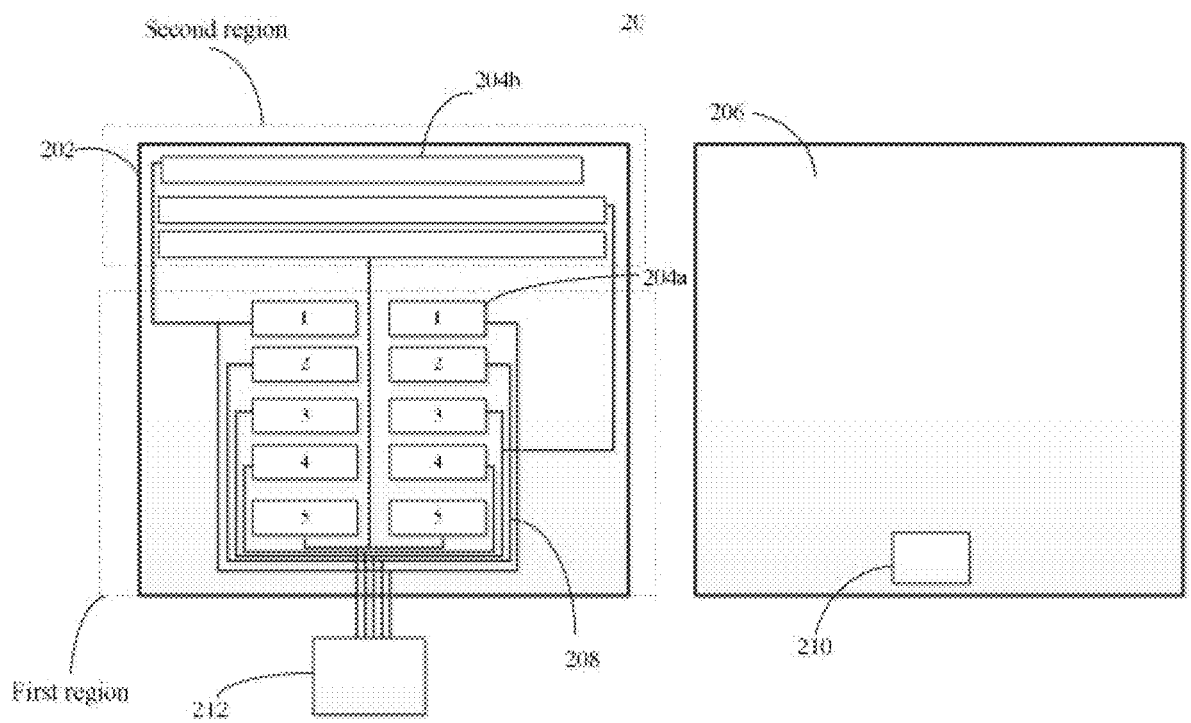
FIG. 13 is a schematic view of a soft physiotherapy instrument according to a second embodiment.

Referring to FIG. 13, a soft physiotherapy instrument 20 according to a second embodiment is provided. The soft physiotherapy instrument 20 comprises a flexible sheet (not labeled) and a controller 212. The flexible sheet includes a first flexible layer 202 and a second flexible layer 206, the first flexible layer 202 and the second flexible layer 206 are stacked with each other. The flexible sheet further includes a plurality of functional layers 204 sandwiched between the first flexible layer 202 and the second flexible layer 206 and a plurality of electrodes 208 electrically connected with the plurality of functional layers 204. The plurality of functional layers 204 includes a plurality of first functional layers 204a located in a first region and a plurality of second functional layers 204b located in a second region. Each of the plurality of electrodes 208 is electrically connected with a pair of first functional layers 204a, and is electrically connected with a second functional layer 204b. In the embodiment according to FIG. 13, the plurality of functional layers 204 includes ten first functional layers 204a symmetrically distributed in the first region, and include three functional layers 204b in the second region. The ten first functional layers 204b include five pairs of first functional layers 204b, and each pair of first functional 204b is numbered 1, 2, 3, 4 and 5 in order from top to bottom of the flexible sheet. The electrodes electrically connected with the five pairs of first functional layers 204a is numbered 1, 2, 3, 4 and 5, which is the same as the number of the first functional layers 204a. The three second functional layers 204b are electrically connected with the three electrodes numbered 1, 3 and 5. That is, a difference of the number x and y of the adjacent second functional layers 204b is 2.

Other characteristics of the soft physiotherapy instrument in the second embodiment are the same as that of the soft physiotherapy instrument in the first embodiment.

Figure 14:
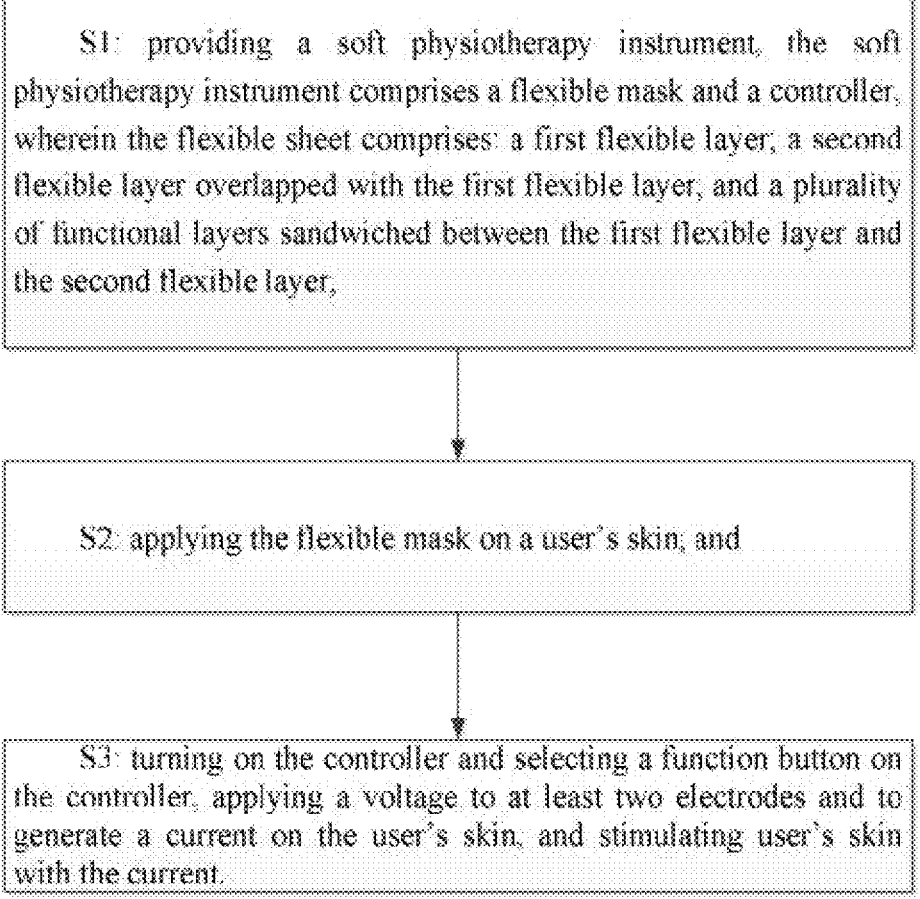
FIG. 14 is a flow chart according to one embodiment showing a method for using a soft physiotherapy instrument.

Referring to FIG. 14, the present disclosure further provides a method of using a soft physiotherapy instrument, the method comprises the steps of:

Step S1: providing a soft physiotherapy instrument, the soft physiotherapy instrument comprises a flexible sheet and a controller;

Step S2: applying the flexible sheet on a user's skin; and

Step S3: turning on the controller and selecting a function button on the controller, inputting a voltage to a plurality of functional layer in the flexible sheet, at least one loop is formed to generate current to stimulate skin of the user.

In step S1, the soft physiotherapy instrument is any one of the soft physiotherapy instruments 10, 20 and 30 discussed above.

Alternatively, before step S2, the flexible sheet can be further infiltrated with a liquid, that is, before the flexible sheet of the soft physiotherapy instrument is applied on the user's skin. The liquid can be a medicine liquid.

In step S3, the controller includes a plurality of function buttons for controlling the flexible sheet. Each of the plurality of function buttons is used to control the functional layer inside the flexible sheet to achieve the stimulating function. Each of the plurality of function buttons can be configured to control a current magnitude, a current frequency, a position of the functional layer which the current is input. The voltage applied on each two electrodes can be kept for a power-on time, and the voltage is stop for a dwell time, then the voltage is applied to another two electrodes for another power-on time and another dwell time.

In step S3, the voltage is applied between the two electrodes in cycles of 1 and 2, 2 and 3, 3 and 4 . . . K−1 and K, so as to circulate the two pairs of first functional layers corresponding to each two electrodes. A loop is formed between the controller, the two electrodes, two pairs of first functional layers, the skin of the user between the two first functional layers on one side, the skin of the user between the two first functional layers on the other side. A current is generated in the loop, as such, the skin of the user between the two first functional layers on one side and the skin of the user between the two first functional layers on the other side in the first region are stimulated. The two electrodes 108 with two neighbor number, e.g., K−1 and K, are connected with the two pairs of first functional layer 104a with two neighbor number, e.g., K−1 and K. And there is no other functional layer 104a located between the adjacent functional layers on the same side. The user's skin located between the adjacent functional layers is stimulated. In this way, by sequentially or selectively applying voltage to the two electrodes 108 with adjacent numbers, the purpose of sequentially or selectively stimulating the skin of the user at different positions in the first region can be achieved.

The controller can also input a voltage between two electrodes that are not adjacent in number. When the difference between the numbers x and y of the two electrodes is greater than or equal to 2, the two pairs of first function layers corresponding to the two electrodes comprises two first functional layers on the same side separated with each other. The two first functional layers on the same side is separated by at least one first functional layer on the same side of the flexible sheet. Even if a loop is formed between the controller, the two electrodes, two pairs of first functional layers, the skin of the user between the two first functional layers on one side, the skin of the user between the two first functional layers on the other side, since the two first functional layers are farther apart on the same side of the flexible sheet, the skin between the two first functional layer has a large area, the electrical resistance of the skin is relatively large, and the current generated at this time will be very small, and the user basically cannot feel it. On the other hand, when the two electrodes numbered x and y are respectively connected to two second functional layers, input voltage on the two electrodes, then another loop is formed between the two electrodes, the two second functional layers, the facial skin between the two second functional layers and the controller. Since the two electrically connected second functional layers 104b are adjacent to each other, the current value is relatively large, which can stimulate the skin between the two secondary functional layers in the second region. As such, the skin in the second region is stimulated. Therefore, when the controller chooses to apply a voltage between two electrodes that are not adjacent to the number, it will not stimulate the skin between the first functional layers in the first region, but it can stimulate the skin between the second functional layers in the second region.

In one embodiment according to FIG. 2, in use of the soft physiotherapy instrument, the electrodes 108 are energized according to the circulation pattern of the electrodes numbered 1 and 2, 2 and 3, and 3 and 4, thereby sequentially or selectively generating micro-currents in the two pairs of first functional layers, which in turn stimulate the skin in the first region. In this embodiment, the power-on time of each pair of electrodes 108 is 1 s and the dwell time is 1 s. That is, with a cycle of 2 s, the power is first applied for 1 s, and then stopped for 1 s, and this cycle is performed. Among them, the voltage applied on each two electrodes is in a range of 20V-36V and the frequency of the voltage is 90 Khz.

Compared with the prior art, the soft physiotherapy instrument provided by the present invention has the following advantages: first, it can directly fit on a user's skin without the need to hold it by hand, which frees the user's hands. Secondly, through controlling a circuit by the controller, the skin on the user's skin can be selectively stimulated, and the skin parts to be stimulated can be selected more accurately without causing facial asymmetry. Third, the carbon nanotube layer is used as the functional layer, the carbon nanotube layer has a better flexibility than the first flexible layer or/and the second flexible layer, and the flexibility of the entire flexible sheet will not be reduced due to the setting of the functional layers, the flexible sheet can fit on the user's skin well, and the user has a high comfort degree. Fourth, the carbon nanotube layer is used as a functional layer, a strength of the carbon nanotube layer is relatively large, no matter how to bend and pull or clean the flexible sheet, the carbon nanotube layer will not be damaged, and the flexible sheet has a long life.

Depending on the embodiment, certain blocks/steps of the methods described may be removed, others may be added, and the sequence of blocks may be altered. It is also to be understood that the description and the claims drawn to a method may comprise some indication in reference to certain blocks/steps. However, the indication used is only to be viewed for identification purposes and not as a suggestion as to an order for the blocks/steps.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A soft physiotherapy instrument, comprising:
a flexible sheet and a controller configured to control the flexible sheet, the flexible sheet comprises:
a first flexible layer;
a second flexible layer overlapped with the first flexible layer;
a plurality of functional layers sandwiched between the first flexible layer and the second flexible layer, wherein the plurality of functional layers comprises K pairs of first functional layers symmetrically located in a first region and M second functional layers located in a second region, the K pairs of first functional layers are labeled 1, 2 . . . K, adjacent two pairs of first functional layers located adjacent with each other are labeled with two adjacent numbers K−1 and K, wherein K≥3, and K is an integer;
K electrodes, each of the K electrodes is electrically connected with a first functional layer of the plurality of functional layers and has a number the same as the first functional layer of the plurality of functional layers, and each of the M second functional layers is electrically connected with an electrode of the K electrodes, adjacent second functional layers are electrically connected with two electrode of the K electrodes with different number x and y, and a difference between x and y is greater than or equal to 2.

2. The soft physiotherapy instrument of claim 1, wherein the first flexible layer or the second flexible layer defines a window, and the K electrodes are exposed from the window and electrically connected to the controller.

3. The soft physiotherapy instrument of claim 1, wherein a material of the first flexible layer or the second flexible layer is non-woven fabric, silk, flexible cloth, porous flexible paper, or silica gel.

4. The soft physiotherapy instrument of claim 1, wherein each of the plurality of functional layers comprises a carbon nanotube layer.

5. The soft physiotherapy instrument of claim 4, wherein the carbon nanotube layer comprises a carbon nanotube film or a plurality of carbon nanotube films overlapped with each other.

6. The soft physiotherapy instrument of claim 5, wherein the carbon nanotube film is a freestanding film.

7. The soft physiotherapy instrument of claim 6, wherein the carbon nanotube film comprises a plurality of successive and oriented carbon nanotubes joined end-to-end by van der Waals attractive force therebetween.

8. The soft physiotherapy instrument of claim 7, wherein the carbon nanotube film comprises a plurality of successively oriented carbon nanotube segments joined end-to-end by van der Waals attractive force therebetween, and each carbon nanotube segment comprises a plurality of carbon nanotubes substantially parallel to each other, and joined by van der Waals attractive force therebetween.

9. The soft physiotherapy instrument of claim 6, wherein the carbon nanotube film comprises a plurality of carbon nanotubes entangled with each other.

10. The soft physiotherapy instrument of claim 6, wherein the carbon nanotube film comprises a plurality of carbon nanotubes joined by van der Waals attractive force, an angle between a primary alignment direction of the carbon nanotubes and a surface of the carbon nanotube film is ranged from 0 degrees to 15 degrees.

11. The soft physiotherapy instrument of claim 4, wherein the carbon nanotube layer comprises at least one carbon nanotube wire, the at least one carbon nanotube wire comprises a plurality of successive carbon nanotube segments joined end to end by van der Waals attractive force therebetween and oriented along a length direction of the at least one carbon nanotube wire.

12. The soft physiotherapy instrument of claim 11, wherein the carbon nanotube layer comprises one carbon nanotube wire, the carbon nanotube wire is bent to form the carbon nanotube layer.

13. The soft physiotherapy instrument of claim 11, wherein the carbon nanotube layer comprises a plurality of carbon nanotube wires crossed or woven with each other.

14. The soft physiotherapy instrument of claim 1, wherein a material of the K electrodes is metal, alloy, indium tin oxide (ITO), antimony tin oxide (ATO), conductive silver paste, conductive polymer or conductive carbon nanotube.

15. The soft physiotherapy instrument of claim 1, wherein the plurality of functional layers is worn by a user at a forehead position, a cheek position, a below an eye position, or a nose position.

16. The soft physiotherapy instrument of claim 1, wherein K is greater than or equal to M.

* * * * *